(12) United States Patent
Busch, Jr. et al.

(10) Patent No.: US 7,927,582 B2
(45) Date of Patent: Apr. 19, 2011

(54) METHOD AND COMPOSITION FOR PRODUCING ENHANCED FINGERNAILS

(75) Inventors: Francis Busch, Jr., Southbury, CT (US); Karen A. Bollert, Trumbull, CT (US)

(73) Assignee: ProStrong, Inc., Cohasset, MA (US)

( * ) Notice: Subject to any disclaimer, the term of this patent is extended or adjusted under 35 U.S.C. 154(b) by 769 days.

(21) Appl. No.: 11/903,418

(22) Filed: Sep. 21, 2007

(65) Prior Publication Data

US 2008/0019931 A1 Jan. 24, 2008

Related U.S. Application Data

(63) Continuation-in-part of application No. 10/890,727, filed on Jul. 14, 2004, now abandoned.

(51) Int. Cl.
- *A61K 8/00* (2006.01)
- *A61K 8/18* (2006.01)
- *A61Q 3/02* (2006.01)

(52) U.S. Cl. ......... 424/61; 424/400

(58) Field of Classification Search ......... None
See application file for complete search history.

(56) References Cited

U.S. PATENT DOCUMENTS

| 6,200,553 | B1 * | 3/2001 | Busch, Jr. .......... 424/61 |
| 6,517,863 | B1 * | 2/2003 | LaTorre et al. .......... 424/447 |

* cited by examiner

*Primary Examiner* — Robert A Wax
*Assistant Examiner* — Melissa S Mercier
(74) *Attorney, Agent, or Firm* — Salter & Michaelson

(57) ABSTRACT

A method for increasing the strength, thickness and surface smoothness of a finger nail composed primarily of keratin but also containing small amount of calcium.

11 Claims, No Drawings

METHOD AND COMPOSITION FOR PRODUCING ENHANCED FINGERNAILS

CROSS REFERENCE TO COPENDING APPLICATIONS

This application is a continuation in part of application having the same title, Ser. No. 10/890,727 filed Jul. 14, 2004 now abandoned.

FIELD OF THE INVENTION

This invention employs methods and compositions for producing enhanced fingernails and toe nails.

BACKGROUND OF THE INVENTION

Fingernails and toe nails are composed primarily of a keratin matrix that includes their exposed surfaces and also contains a small amount of calcium and other chemical elements.

Human beings desire strong healthy nails for both cosmetic and medical reasons. However, some nails in normal use may crack and break and various treatments have become available to ameliorate these conditions.

U.S. Pat. No. 5,478,551 discloses that such nails can be strengthened and thus be prevented from cracking and breaking by using a fluoride treatment, since fluorides combine with the calcium present in the nails to form a reinforced keratin matrix. This type of treatment works well if the quantity of naturally occurring calcium is sufficient. Nevertheless, it generally takes about thirty days for optimum results and this treatment does not work well if there is not enough calcium present.

Subsequently, it has been found that when an application of a calcium material precedes the fluoride nail treatment, the nail strength is increased to the level of nails having a sufficient about of naturally occurring calcium. Using this method, the nail strength is increased but two successive separate steps are employed and the improvements occur gradually to reach a maximum level in about thirty days.

Moreover this two step treatment does not increase the thickness of thin fingernails. There is considerable variation in nail thickness found in nails subjected to the two step treatment. Applicants have observed that normal nail thickness can vary from a minimum of perhaps 0.005 inches to a maximum of perhaps 0.0300 inches. The thinner nails are the first to break.

The present invention is directed toward compositions and methods which produce increased nail thickness and stronger nails. The nails so produced also display smoother exposed surfaces.

SUMMARY OF THE INVENTION

It is an object of the present invention to provide new methods and compositions which when applied to nails produces stronger nails with increased nail thickness.

Another object is to provide such new methods and compositions which do not employ fluoride compounds with or without prior calcium treatment.

Still another object is to provide new methods and compositions which when applied to nails not only produce stronger nails of increased thickness but also produce nails with smoother exposed surfaces.

These and other objects and advantages of this invention will either be explained or will become apparent hereinafter In accordance with the principles of this invention, compounds containing both calcium and phosphorous ions are applied to the nail. The nail so treated was found to be stronger and thicker. In addition, surprisingly, the nail was found to display a smoother external surface.

These compounds include Calcium Fluorophosphate, Calcium Hypophosphate, Calcium Glycerophosphate and preferably Calcium Phosphate Monobasic. All these compounds are soluble in water and can be incorporated into cosmetically acceptable vehicles In order to use these calcium phosphorous compounds in nail treatment, it is first necessary to dissolve them in a suitable solvent or incorporated into a cosmetically acceptable gel, paste or cream. These aforementioned compounds crystallize on the nail surface in the presence of keratin, causing remineralization of the nail and thus provides the enhanced nail characteristics of increased thickness, strength and smoothness.

The compounds can be formed into gels, pastes or creams employing cosmetic emulsion technology well known in the art.

Examples of Preparing Calcium Phosphorous Compounds in Cream Form

The following examples of such a cream are as follows as shown in parts per weight: There are four examples, each being a different vertical column numbered 1 through 5 respectively.

|  | 1 | 2 | 3 | 4 | 5 |
|---|---|---|---|---|---|
| WATER PHASE | | | | | |
| De-ionized water | 76.90 | 77.40 | 77.70 | 76.90 | 76.90 |
| Ethoxydigylcol | 3.00 | 3.00 | 3.00 | 3.00 | 3.00 |
| Glycerin | 3.50 | 3.50 | 3.50 | 3.50 | 3.50 |
| NaOH, 10% solution | 0.70 | 0.70 | 0.70 | 0.70 | 0.70 |
| Calcium Phosphate, monobasic | 1.00 | .50 | — | — | — |
| Calcium Fluorophophate | — | — | 0.20 | — | — |
| Calcium Hyprohosphite | — | — | — | 1.00 | — |
| Calcium Glycerophosphate | — | — | — | — | 1.00 |
| OIL PHASE | | | | | |
| Crodafos CES | 4.0 | 4.0 | 4.0 | 4.0 | 4.0 |
| Volpo S-2 | 0.40 | 0.40 | 0.40 | 0.40 | 0.40 |
| Volpo S-10 | 1.20 | 1.20 | 1.20 | 1.20 | 1.20 |
| Crodamol PMP | 7.00 | 7.00 | 7.00 | 7.00 | 7.00 |
| DC 344 Fluid | 2.00 | 2.00 | 2.00 | 2.00 | 2.00 |
| Nipastat | 0.30 | 0.30 | 0.30 | 0.30 | 0.30 |

The first four ingredients of the oil phase are available commercially from Croda USA; Nipastat from Nipa; and DC 344 Fluid from Dow Corning. The other ingredients are standard cosmetic ingredients widely used and well known in the art and are used for their normal purpose in forming an acceptable cosmetic cream. Various concentrations of the calcium, phosphorous compounds of this invention have demonstrated to effectively increase the thickness and strength of the fingernails.

The preferred calcium, phosphorous phases of this invention are solutions of the calcium, phosphorous compounds in a gel. The following examples of such solutions are as follows shown in parts per weight: There are four examples each being a different column numbered 6 through 10 respectively.

|  | 6 | 7 | 8 | 9 | 10 |
|---|---|---|---|---|---|
| De-ionized Water | 89.60 | 89.60 | 90.40 | 90.10 | 89.60 |
| Propylene Glycol | 8.00 | 8.00 | 8.00 | 8.00 | 8.00 |
| Calcium Phosphate Monobasic | 1.00 | — | — | 0.50 | — |
| Calcium Hypophoshite | — | 1.00 | — | — | — |
| Calcium Fluorophosphate Dihydrate | — | — | 0.20 | — | — |
| Calcium Glycerophosphate | — | — | — | — | 1.00 |
| Natrosol 250 HHRCS | 1.00 | 1.00 | 1.00 | 1.00 | 1.00 |
| Methylparaben | 0.20 | 0.20 | 0.20 | 0.20 | 0.20 |
| Imidazolidinyl Urea | 0.20 | 0.20 | 0.20 | 0.20 | 0.20 |

The Natrosol 250 HHRCS is commercially available from Hercules. The other ingredients are standard cosmetic ingredients widely used and well known in the art.

Test Results

Two in vivo evaluations were made to determine the effects of treating fingernails with a gel containing 1.0% calcium phosphate monobasic. Before any treatment occurred, the fingernails were photographed and initial measurements were recorded.

The First Evaluation

First nail strength was measured on the nails of five healthy subjects. In order to measure nail strength, a platform was used which positions the fingernail over a flattened cylinder. The cylinder creates a gap resulting from the curve of the nail and remains constant from week to week. Since the distance form the nail to the top of the flattened cylinder remains constant, the force required to bend the nail flat against the flattened cylinder remains constant, the force required to bend the nail flat against the flattened cylinder can then be easily measured using a WAGNER force gauge. The gauge indicates the force required to bend the nail a constant distance in grams per square inch. Subjects applied the gel once a day for six weeks.

|  | Average Nail Strength Initial | Average Nail Strength 1 week | % Change |
|---|---|---|---|
| Subject One | 210 | 415 | +98% |
| Subject Two | 288 | 447 | +55% |
| Subject Three | 255 | 330 | +29% |
| Subject Four | 133 | 269 | +102% |

|  | Average Nail Strength Initial | Average Nail Strength 6 weeks | % Change |
|---|---|---|---|
| Subject One | 210 | 520 | +148% |
| Subject Two | 288 | 360 | +25% |
| Subject Three | 255 | 429 | +68% |
| Subject Four | 133 | 315 | +137% |

The above listed results demonstrate an average increase in fingernail strength of 71% after one week of use and 94.5% after six weeks.

The Second Evaluation

The second evaluation demonstrated a significant increase in fingernail thickness between before and after measurements. 20 healthy subjects applied the above mentioned gel, waited ten minutes, washed and dried their nails. The nails were measured using a Fowler & NSK electronic digital caliper.

The data lend itself to a paired or related sample study design since the same subjects were observed under two conditions-before treatment and after. The hypothesis is that use of the test product will increase fingernail thickness. The null hypothesis is there is no difference in fingernail thickness. The non-parametric Wilcoxon matched-pair signed-rank test was used to test the hypothesis.

Non-Parametric Wilcoxon Matched-Pair Signed-ranks Test

| Descriptive Statistics | | | | | |
|---|---|---|---|---|---|
|  | N | Mean | Std. Deviation | Minimum | Maximum |
| Before | 196 | .02014 | .006793 | .006 | .042 |
| After | 196 | .02222 | .007086 | .010 | .042 |

| Ranks | | | | |
|---|---|---|---|---|
|  |  | N | Mean Rank | Sum of Ranks |
| After - Before | Negative Ranks | 61[a] | 74.38 | 4537.00 |
|  | Positive Ranks | 113[b] | 94.58 | 10688.00 |
|  | Ties | 22[c] |  |  |
|  | Total | 196 |  |  |

[a]After < Before
[b]After > Before
[c]After = Before

| Test Statistics[b] | |
|---|---|
|  | After - Before |
| Z | −4.630[a] |
| Asymp. Sig. (2-tailed) | .000 |

[a]Based on negative ranks.
[b]Wilcoxon Signed Ranks Test

The findings demonstrate that a statistically significant difference existed between the before and after product treatment groups. The results are significant at the 99% level of confidence and demonstrate that the use of this product increases fingernail thickness. The above analysis of the data shows an increase in the mean of the after measurements of 10%. The subjects' fingernail thickness increased an average of 10%.

The panelists after treatment also completed a questionnaire as shown below.

| NAIL SERUM QUESTIONNAIRE |
|---|
| 1. DOES YOUR NAILS FEEL SMOOTHER?<br>95% YES<br>5% NO |

-continued

NAIL SERUM QUESTIONNAIRE

2. DO YOUR RIDGES LOOK BETTER?
   95% YES
   5% NO
3. DID YOU SEE AN IMPROVEMENT IN THE APPEARANCE OF YOUR NAILS?
   95% YES
   5% NO
4. DO YOUR NAILS APPEAR?
   HEALTHIER 79%
   THICKER 79%
   THINNER 0%
   OTHER 0%

While the invention has been described with special attention to the test results, the protection solicited is to be limited only by the terms of the claims which follow.

What is claimed is:

1. A method for treating keratin finger and toe nails to increase their strength and thickness comprising the steps of:
applying a calcium phosphorous salt in a suitable vehicle to the surface of the nail to be treated;
wherein the step of applying the calicum phosphorous salt to the surface of the nail includes forming both calcium phosphorous ions that are applied to the nail surface;
causing the material to remain in contact with this nail surface until the material crystallizes on the surface and produces a remineralization of the keratin matrix of the nail, said remineralization increasing the nail strength and thickness;
and wherein the applying step is a single step.

2. The method of claim 1 wherein the crystallization is produced in about ten minutes, 3. A calcium phosphorous salt used as a vehicle in treating keratin finger and toe nails to produce remineralization of the keratin matrix of the nail producing thicker nails, the salt being selected from the group consisting of calcium phosphate monobasic, calcium fluorophosphates, calcium hypophosphite, and calcium glycerophosphate.

4. The method of claim 3 wherein the sufficient period can have a minimum value of ten minutes, 5. The method of claim 4 wherein the treated nail also becomes stronger and smoother.

6. A method for increasing the strength, thickness and surface smoothness of a finger nail composed primarily of keratin but also containing small amount of calcium by produchig calcium and phosphorous ions in the form of a liquid, cream or paste and applying said ions so formed to the nail surface for a period of time on the order of ten minutes so that the ions crystallize on the surface and cause the nail to remineralize.

7. The method of claim 1 wherein the calcium phosphate salt is provided in a range on the order of 0.20 to 1.0 parts per total weight.

8. The method of claim 1 wherein, after the step of applying the calcium phosphate salt, no further step of applying a fluoride salt occurs.

9. A method for treating keratin finger and toe nails to increase their strength and thickness, said method consisting essentially of the steps of:
applying a calcium phosphorous salt in a suitable vehicle to the surface of the nail to be treated;
wherein the step of applying the calcium phosphorous salt to the surface of the nail includes forming both calcium and phosphorous ions that are applied to the nail surface;
causing the material to remain in contact with this nail surface until the material crystallizes on the surface and produces a remineralization of the keratin matrix, of the nail, said remineralization increasing the nail strength and thickness.

10. The method of claim 9 wherein the calcium phosphate salt is provided in a range on the order of 0.20 to 1.0 parts per total weight.

11. The method of claim 9 wherein the crystallization is produced in about ten minutes.

\* \* \* \* \*